United States Patent
Avery

(10) Patent No.: US 10,463,599 B2
(45) Date of Patent: Nov. 5, 2019

(54) HAIR CARE COMPOSITION COMPRISING POLYDIMETHYLSILOXANE POLYMER EMULSION

(71) Applicant: Conopco, Inc., Englewood Cliffs, NJ (US)

(72) Inventor: Andrew Richard Avery, Ellesmere Port (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 22 days.

(21) Appl. No.: 15/504,529

(22) PCT Filed: Aug. 26, 2015

(86) PCT No.: PCT/EP2015/069540
§ 371 (c)(1),
(2) Date: Feb. 16, 2017

(87) PCT Pub. No.: WO2016/041748
PCT Pub. Date: Mar. 24, 2016

(65) Prior Publication Data
US 2017/0231897 A1    Aug. 17, 2017

(30) Foreign Application Priority Data

Sep. 15, 2014 (EP) .................... 14184731

(51) Int. Cl.
| A61K 8/898 | (2006.01) |
| A61Q 5/12 | (2006.01) |
| A61K 8/34 | (2006.01) |
| A61K 8/31 | (2006.01) |
| A61K 8/06 | (2006.01) |
| A61K 8/41 | (2006.01) |
| A61K 8/44 | (2006.01) |
| A61K 8/891 | (2006.01) |
| A61K 8/02 | (2006.01) |
| A61K 8/04 | (2006.01) |

(52) U.S. Cl.
CPC ............ *A61K 8/898* (2013.01); *A61K 8/0295* (2013.01); *A61K 8/042* (2013.01); *A61K 8/06* (2013.01); *A61K 8/31* (2013.01); *A61K 8/342* (2013.01); *A61K 8/442* (2013.01); *A61K 8/891* (2013.01); *A61Q 5/12* (2013.01); A61K 8/416 (2013.01)

(58) Field of Classification Search
None
See application file for complete search history.

(56) References Cited

U.S. PATENT DOCUMENTS

| 9,976,105 B2 | 5/2018 | Barnes et al. |
| 2011/0243870 A1 | 10/2011 | Cooke et al. |
| 2012/0093757 A1 | 4/2012 | Murray et al. |

FOREIGN PATENT DOCUMENTS

| CN | 101522758 | 9/2009 |
| CN | 102209577 | 10/2011 |
| CN | 102448427 | 5/2012 |
| WO | WO2005079730 | 9/2005 |
| WO | WO2006045427 | 5/2006 |
| WO | WO20100136285 | 12/2010 |
| WO | WO2013092118 | 6/2013 |
| WO | WO2014016350 | 1/2014 |

OTHER PUBLICATIONS

IRPR2 in PCTEP2015069540, Sep. 21, 2016.
Search Report in EP14184731, dated Apr. 30, 2015, EP.
Search Report in PCTEP2015069540, dated Nov. 23, 2015.
Written Opinion in EP14184731, dated Apr. 30, 2015, EP.
Written Opinion in PCTEP2015069540, dated Nov. 23, 2015.

*Primary Examiner* — Nicole P Babson
(74) *Attorney, Agent, or Firm* — Foley & Lardner LLP

(57) ABSTRACT

The invention provides a hair care composition obtainable by blending a conditioning gel phase with an aqueous polydimethylsiloxane polymer emulsion; the conditioning gel phase being formed from a cationic surfactant, a high melting point (25° C. or higher) fatty compound and an aqueous carrier; and the aqueous polydimethylsiloxane polymer emulsion having an aqueous continuous phase consisting of water and a blend of nonionic and cationic surfactants and a dispersed phase consisting of a polydimethylsiloxane polymer and a hydrocarbon oil, wherein the polydimethylsiloxane polymer has a dynamic viscosity of 50,000 to 110,000 cP at 25° C., and the hydrocarbon oil has a kinematic viscosity of 1 to 35 cSt at 40° C. and a specific gravity of 0.76 to 0.87 at 25° C., and the weight ratio of the polydimethylsiloxane polymer to the hydrocarbon oil is 45:55 to 70:30.

18 Claims, No Drawings

HAIR CARE COMPOSITION COMPRISING POLYDIMETHYLSILOXANE POLYMER EMULSION

FIELD OF THE INVENTION

This invention relates to hair care compositions containing a high viscosity polydimethylsiloxane polymer emulsion.

BACKGROUND OF THE INVENTION AND PRIOR ART

Shampooing cleans the hair by removing excess soil and sebum. However, shampooing can leave the hair in a wet, tangled, and generally unmanageable state. Once the hair dries, it is often left in a dry, rough, lustreless, or frizzy condition due to removal of the hair's natural oils and other natural conditioning and moisturizing components. A variety of approaches have been developed to condition the hair. A common method of providing conditioning benefits to the hair is through the use of conditioning agents such as cationic surfactants and polymers, high melting point fatty compounds, low melting point oils, silicone compounds, and mixtures thereof.

Despite the prior art, there still exists the opportunity to increase the conditioning benefits delivered through hair care compositions. A particular need exists for hair care compositions which can deliver enhanced hair shaping benefits such as hair strand alignment, frizz control and manageability.

The present invention provides a conditioning composition with superior conditioning capability.

SUMMARY OF THE INVENTION

The present invention provides a hair care composition obtainable by blending a conditioning gel phase with an aqueous polydimethylsiloxane polymer emulsion;
the conditioning gel phase being formed from a cationic surfactant, a high melting point (25° C. or higher) fatty compound and an aqueous carrier;
and the aqueous polydimethylsiloxane polymer emulsion having an aqueous continuous phase consisting of water and a blend of nonionic and cationic surfactants and a dispersed phase consisting of a polydimethylsiloxane polymer and a hydrocarbon oil, wherein the polydimethylsiloxane polymer has a dynamic viscosity of 50,000 to 110,000 cP at 25° C., and the hydrocarbon oil has a kinematic viscosity of 1 to 35 cSt at 40° C. and a specific gravity of 0.76 to 0.87 at 25° C., and the weight ratio of the polydimethylsiloxane polymer to the hydrocarbon oil is 45:55 to 70:30.

DETAILED DESCRIPTION OF THE INVENTION

Conditioning Gel Phase

Examples of suitable cationic surfactants which are useful for forming the conditioning gel phase include quaternary ammonium cationic surfactants corresponding to the following general formula:

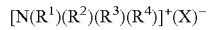

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably $CH_3$.

Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Alternatively, primary, secondary or tertiary fatty amines may be used in combination with an acid to provide a cationic surfactant suitable for providing the conditioning gel phase suitable for use in the invention. The acid protonates the amine and forms an amine salt in situ in the hair care composition. The amine is therefore effectively a non-permanent quaternary ammonium or pseudo-quaternary ammonium cationic surfactant.

Suitable fatty amines of this type include amidoamines of the following general formula:

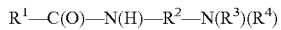

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms.

Specific examples of suitable materials of the above general formula are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

The acid used may be any organic or mineral acid which is capable of protonating the amine in the hair care composition. Suitable acids include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

Mixtures of any of the above-described cationic surfactants may also be suitable.

The level of cationic surfactant suitably ranges from 0.1 to 10 wt %, preferably from 0.2 to 5 wt % and more preferably from 0.25 to 4 wt % (by total weight of cationic surfactant based on the total weight of the hair care composition).

By "high melting point" in the context of this invention is generally meant a melting point of 25° C. or higher. Generally the melting point ranges from 25° C. up to 90° C., preferably from 40° C. up to 70° C. and more preferably from 50° C. up to about 65° C.

The high melting point fatty compound can be used as a single compound or as a blend or mixture of at least two high melting point fatty compounds. When a blend or mixture of fatty compounds is used, the melting point means the melting point of the blend or mixture.

Suitable fatty compounds of this type have the general formula R—X, wherein R is an aliphatic carbon chain and X is a functional group (e.g. alcohol or carboxylic acid or a derivative thereof such as ester or amide).

R is preferably a saturated aliphatic carbon chain comprising from 8 to 30 carbon atoms, preferably from 14 to 30 carbon atoms, more preferably from 16 to 22 carbon atoms.

R can contain, in addition to carbon and hydrogen atoms, ether linkages, and other groups such as amino groups. Preferably R is a linear alkyl chain comprising from 8 to 30 carbon atoms, preferably from 14 to 30 carbon atoms, more preferably from 16 to 22 carbon atoms.

X is preferably an —OH group.

Most preferably, the fatty compound is a fatty alcohol of general formula $CH_3(CH_2)_n OH$, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty compounds may also be suitable.

The level of fatty compound suitably ranges from 0.01 to 10 wt %, preferably from 0.1 to 8 wt %, more preferably from 0.2 to 7 wt % and most preferably from 0.3 to 6 wt % (by total weight of fatty compound based on the total weight of the hair care composition).

The weight ratio of cationic surfactant to fatty compound is suitably from 1:1 to 1:10, preferably from 1:1.5 to 1:8, optimally from 1:2 to 1:5.

Conditioning gel phases suitable for use in the invention may be characterized as gel ($L_\beta$) surfactant mesophases consisting of surfactant bilayers.

In a general process for the preparation of such conditioning gel phases, the cationic surfactant, high melting point fatty compound and aqueous carrier are heated to form a mixture, which is cooled under shear to room temperature. The mixture undergoes a number of phase transitions during cooling, normally resulting in a gel ($L_\beta$) surfactant mesophase consisting of surfactant bilayers. The bilayers may grow, swell or fold to form extended sheets or spherical vesicles.

Preferably, the formation of the gel ($L_\beta$) surfactant mesophase is controlled by maintaining the temperature of the mixture so that it falls within a specified range, generally from about 55 to about 67° C., in the mixing vessel.

In an example of such a preferred process, the fatty compound and the cationic surfactant may be "comelted" in a first vessel to form an isotropic phase. The comelt will typically comprise from 45 to 90 wt % fatty alcohol of general formula $CH_3(CH_2)_n OH$, where n is an integer from 7 to 29, preferably from 15 to 21; from 10 to 40 wt % cationic surfactant of general formula $[N(R^1)(CH_3)_3]^+(X)^-$, where $R^1$ is a $C_{16}$ to $C_{22}$ saturated alkyl chain and X is halide;

and from 0 to 15 wt % water (by weight based on the total weight of the comelt). The comelt in the first vessel is typically maintained at a temperature sufficient to maintain the fatty compound in a liquid phase (usually around 80 to 85° C.). The comelt is then added to a second vessel containing water at about 50 to about 60° C., and the comelt and the water are mixed. In the second vessel, the temperature of the mixture of the comelt and the water is controlled such that it is maintained at from 56 to 65° C., preferably from 58 to 62° C., more preferably around 60° C. The cationic surfactant component of the comelt as described above may also comprise or consist of a fatty amidoamine of general formula:

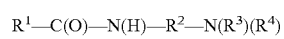

$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms. In this case the water in the second vessel will suitably include from 0.01 to 3 wt % of an organic or mineral acid which is capable of protonating the fatty amidoamine.

In an alternative example of a preferred process, a 'comelt' (such as described above) and water may be independently added to a mixing vessel and mixed in a continuous process in which the temperature of the mixture of comelt and water is controlled by modifying the temperature of water added to the mixture. Water may be added in a single dose or in aliquots. Typically, a first water vessel is maintained at around 40° C. and is pumped into the mixing vessel while a second water vessel is maintained at a sufficient temperature to modify the temperature of the mixture of water with comelt such that it falls within the required range as specified above.

In another example of a preferred process, the fatty compound and the cationic surfactant may be combined in an aqueous dispersion. According to this process, an aqueous dispersion is prepared, which dispersion typically comprises from 25 to 50 wt % water, from 4 to 20 wt % fatty alcohol of general formula $CH_3(CH_2)_nOH$, where n is an integer from 7 to 29, preferably from 15 to 21; and from 1 to 5 wt % fatty amidoamine of general formula:

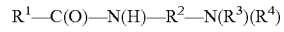

$R^1$—C(O)—N(H)—$R^2$—N($R^3$)($R^4$)

in which $R^1$ is a fatty acid chain containing from 12 to 22 carbon atoms, $R^2$ is an alkylene group containing from one to four carbon atoms, and $R^3$ and $R^4$ are each independently, an alkyl group having from one to four carbon atoms (by weight based on the total weight of the dispersion). Preferably, the temperature of the aqueous dispersion is maintained above the melting temperature of the fatty alcohol, preferably at least 5° C. higher than the melting point of the fatty alcohol. A cationic surfactant of general formula $[N(R^1)(CH_3)_3]^+(X)^-$, where $R^1$ is a $C_{16}$ to $C_{22}$ saturated alkyl chain and X is halide; may then be added and mixed into the aqueous dispersion, generally at a level of from 0.5 to 5 wt % (by weight based on the total weight of the mixture). Preferably the mixing of the cationic surfactant with the aqueous dispersion is monitored by measurement of viscosity, such that when the viscosity change plateaus, mixing is complete (generally after about 20 to 60 minutes of mixing). After mixing is complete, the fatty amidoamine is neutralised with a suitable acid as described above. Preferably, the temperature of the mixture of the aqueous dispersion and the cationic surfactant is maintained at from 56 to 67° C., preferably from 58 to 65° C., more preferably around 63° C. Preferably, the process is a batch process.

Another preferred process for making a conditioning gel phase suitable for use in the invention comprises forming an aqueous isotropic solution of cationic surfactant (typically of general formula $[N(R^1)(CH_3)_3]^+(X)^-$, where $R^1$ is a $C_{16}$ to $C_{22}$ saturated alkyl chain and X is halide); and mixing the aqueous isotropic solution of cationic surfactant with molten fatty compound (typically a fatty alcohol of general formula $CH_3(CH_2)_n$ OH, where n is an integer from 7 to 29, preferably from 15 to 21). Typically, the fatty alcohol is maintained at a temperature sufficient to maintain it in a liquid phase (usually around 80 to 85° C.), prior to its addition to the aqueous isotropic solution of cationic surfactant. Preferably, the temperature of the mixture of the fatty alcohol and aqueous isotropic solution is maintained at from 55° C. to 65° C., more preferably at from 58° C. to 62° C. and most preferably at about 60° C.

Aqueous Silicone Polymer Emulsion

The hair care composition of the invention is obtainable by blending a conditioning gel phase (as described above) with an aqueous polydimethylsiloxane polymer emulsion having an aqueous continuous phase consisting of water and a blend of nonionic and cationic surfactants and a dispersed phase consisting of a polydimethylsiloxane polymer and a hydrocarbon oil, wherein the polydimethylsiloxane polymer has a dynamic viscosity of 50,000 to 110,000 cP at 25° C., and the hydrocarbon oil has a kinematic viscosity of 1 to 35 cSt at 40° C. and a specific gravity of 0.76 to 0.87 at 25° C., and the weight ratio of the polydimethylsiloxane polymer to the hydrocarbon oil is 45:55 to 70:30.

WO2008/045427 describes methods for preparing the aqueous polydimethylsiloxane polymer emulsion of the present invention.

For the purposes of the present invention, the polydimethylsiloxane polymer preferably comprises a degree of branching, which will typically range from about 2 to about 7, more preferably from about 3 to about 6 branches per molecule of polymer.

Suitable hydrocarbon oils in the context of the present invention include saturated, non-polar straight or branched-chain aliphatic or alicyclic hydrocarbons having from about 10 to about 50 carbon atoms, and mixtures thereof.

A preferred hydrocarbon oil in the context of the present invention is light mineral oil. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons, in which the number of carbon atoms per hydrocarbon molecule generally ranges from $C_{10}$ to $C_{40}$.

The mineral oil may be characterised in terms of its viscosity, where light mineral oil is less viscous than heavy mineral oil. A suitable light mineral oil will generally have a kinematic viscosity of 3.9 to 5.0 cSt at 40° C. and a specific gravity of 0.810 to 0.830 at 25° C. Such materials are commercially available under the brand name Lytol™.

The aqueous silicone polymer emulsion for use in the invention has an aqueous continuous phase comprising a blend of a nonionic surfactant and a cationic surfactant such as cetyltrimethylammonium chloride.

The amount of surfactant used will vary depending on the particular surfactant selected, but generally ranges from 0.84 to 2.51% by total weight of surfactant based on the total weight of the aqueous polydimethysiloxane polymer emulsion.

Product Form and Optional Ingredients

The hair care compositions of the invention are primarily intended for topical application to the hair and/or scalp of a human subject in order to improve hair fibre surface properties such as hair fibre lubrication, smoothness, softness, manageability, alignment, and shine.

The hair care compositions of the invention are typically "rinse-off" compositions to be applied to the hair and then rinsed away.

A particularly preferred product form is a conditioner for the treatment of hair (typically after shampooing) and subsequent rinsing.

Generally, such a composition is applied to the hair (preferably hair which has been shampooed and then rinsed with water), and then worked through the hair. Preferably the composition is then left to penetrate the hair for a period of about one to three minutes before rinsing it from the hair with water. Typically, from about 1 g to about 50 g of the composition is applied to the hair or scalp.

The hair care compositions of the invention will generally comprise from about 20% to about 95%, preferably from about 30% to about 92%, and more preferably from about 50% to about 90% water, by weight based on total weight. Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The hair care compositions of the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

The invention will now be further described by reference to the following Examples. In the Examples, all percentages are by weight based on total weight, unless otherwise specified.

EXAMPLES

Example 1

Hair conditioning compositions were prepared, having ingredients as shown in Table 1 below. Example 1 represents a composition according to the invention. Example A is a comparative example (not according to the invention).

TABLE 1

| Ingredient | Example A (% w/w) | Example 1 (% w/w) |
|---|---|---|
| Stearylamidopropyl dimethylamine | 0.3188 | 0.3188 |
| Behentrimonium chloride (70% a.i.) | 1.365 | 1.365 |
| Lactic acid (88% a.i.) | 0.102 | 0.102 |
| Sodium chloride | 0.1 | 0.1 |
| Disodium EDTA | 0.1 | 0.1 |
| Silicone emulsion (70% a.i.)[1] | 4.29 | 0 |
| Cetearyl alcohol | 3.4 | 3.4 |
| PEG 150 distearate | 0.01 | 0.01 |
| Silicone emulsion(50.3% a.i.)[2] | 0 | 5.964 |
| Water, perfume, preservatives | q.s. to 100 | q.s. to 100 |

[1]Emulsion of dimethicone/amodimethicone with cetyl trimethylammonium chloride and water, ex Dow Corning
[2]Emulsion of dimethicone/white mineral oil with cetyl trimethylammonium chloride and water, ex Dow Corning Evaluation The compositions of Example 1 and Example A were evaluated as follows:

Half Head Salon Testing 36 panellists with dry to dry and damaged hair types of mixed length and texture were recruited for the testing in a dedicated salon facility. The test protocol used a stripping shampoo applied to both sides for each panellist, then the compositions were compared in a half head salon test. The compositions were assessed by expert assessors on the attributes detailed in Table 2 below. It will be noted that some attributes can be considered as positive and others negative. In all cases where differences were recorded, Example 1 (according to the invention) scored higher than Example A (not according to the invention) on the positive and lower than Example A on the negative attributes.

TABLE 2

| Use Stage | Attribute | n value | Ex.A Votes | Ex.1 Votes | Significance | p-value |
|---|---|---|---|---|---|---|
| Application | 1-Ease of spread | 33 | 13 | 20 | | 0.223017 |
| Application | 2 -Visual absorbency | 32 | 17 | 15 | | 0.723674 |
| Application | 3-Speed of incorporation | 33 | 17 | 16 | | 0.861804 |
| Application | 4-Ease of detangling with fingers | 27 | 8 | 19 | 0.95 | 0.034264 |
| Application | 5-Product coating | 35 | 11 | 24 | 0.95 | 0.027992 |
| Rinse | 6-Maximum slippery feel | 36 | 4 | 32 | 0.95 | 3.06E−06 |
| Rinse | 7-Longer Time to Rinse | 34 | 11 | 23 | 0.95 | 0.039592 |
| Rinse | 8-Alignment during Rinse | 34 | 10 | 24 | 0.95 | 0.016351 |
| Rinse | 9-Slippery Feel under rinsing | 34 | 5 | 29 | 0.95 | 3.86E−05 |
| Wet stage | 10-Ease of Wet Combing-TE | 34 | 11 | 23 | 0.95 | 0.039592 |
| Wet stage | 11-Ease of Wet Combing-1st | 34 | 12 | 22 | 0.9 | 0.086348 |
| Wet stage | 12-Slippery feel-Wet | 36 | 5 | 31 | 0.95 | 1.47E−05 |
| Wet stage | 13-Residual coating | 36 | 8 | 28 | 0.95 | 0.000858 |
| Dry stage | 14-Ease of Style | 34 | 7 | 27 | 0.95 | 0.000604 |
| Dry stage | 15-Ease of Dry Combing-TE | 35 | 7 | 28 | 0.95 | 0.000386 |
| Dry stage | 16-Ease of Dry Combing-1st | 35 | 10 | 25 | 0.95 | 0.01123 |
| Dry stage | 17-Most Fluffy/Frizzy look | 35 | 28 | 7 | 0.95 | 0.000386 |
| Dry stage | 18-Volume/fullness | 36 | 15 | 21 | | 0.317311 |
| Dry stage | 19-Most Aligned | 35 | 12 | 23 | 0.9 | 0.062979 |
| Dry stage | 20-Coarseness/Roughness | 28 | 23 | 5 | 0.95 | 0.00067 |
| Dry stage | 21-Shine | 29 | 14 | 15 | | 0.852684 |
| Dry stage | 22-Slippery Feel | 35 | 5 | 30 | 0.95 | 2.38E−05 |
| Dry stage | 23-Smooth Feel | 33 | 6 | 27 | 0.95 | 0.000257 |
| Dry stage | 24-Hair dryness | 35 | 28 | 7 | 0.95 | 0.000386 |
| Dry stage | 25-Dry ends | 34 | 26 | 8 | 0.95 | 0.002022 |
| Dry stage | 26-Residual | 29 | 3 | 26 | 0.95 | 1.95E−05 |
| Dry stage | 27-Preferred shape | 34 | 8 | 26 | 0.95 | 0.002022 |

Examples 2 to 6

Hair conditioning compositions were prepared, having ingredients as shown in Table 3 below. Examples 2 to 6 represent compositions according to the invention. Examples B to G are comparative examples (not according to the invention).

TABLE 3

| Ingredient | Example B (% w/w) | Examples C to G (% w/w) | Examples 2 to 6 (% w/w) |
|---|---|---|---|
| Stearylamidopropyl dimethylamine | 1.25 | 1.25 | 1.25 |
| Behentrimonium chloride (70% a.i.) | 1.25 | 1.25 | 1.25 |
| Lactic acid (88% a.i.) | 0.36 | 0.36 | 0.36 |
| Potassium chloride | 0.1 | 0.1 | 0.1 |
| Disodium EDTA | 0.1 | 0.1 | 0.1 |
| Silicone emulsion(70% a.i.)[1] | 3.57 | 3.57 | 3.57 |
| Cetearyl alcohol | 5 | 5 | 5 |
| Silicone emulsion(50% a.i.)[3] | 0 | 0 | 0.5, 1, 2, 3, 4 |
| Silicone emulsion(50% a.i.)[4] | 0 | 0.5, 1, 2, 3, 4 | 0 |
| Water, perfume, preservatives | q.s. to 100 | q.s. to 100 | q.s. to 100 |

[3]Emulsion of dimethicone/isohexadecane with cetyl trimethylammonium chloride and water, ex Dow Corning
[4]Emulsion of dimethicone/sunflower oil with cetyl trimethylammonium chloride and water, ex Dow Corning Evaluation The compositions of Examples 2 to 6 and Examples B to G were evaluated as follows:

Friction Measurements on Dry Hair 2.5 g, 150 mm (6") European Dark Brown hair switches were used to test the frictional properties of example compositions.

For treatment with any example composition, switches were handled in bundles of 5 per product. Switches were first washed with a simple, stripping shampoo comprising sodium lauryl ether sulphate and water, before 2 g of the test product was applied and massaged into the hair bundles for one minute. Rinsing, following massaging was for a further minute under tap water set at 37° C. and flowing at 4 liters per minute. Switches were then individually detangled and combed through before drying at 50° C.

Individual 2.5 g, 150 mm (6") switches (5 per product) were mounted on a flat, metal block. These were held in place using clamps at either end. After fixing one end, each hair switch was combed through. Each switch was held under tension before fixing the second clamp in place, to ensure that fibres remained immobile when a friction probe was passed over them.

Frictional properties of individual switches were measured dry using a texture analyser (Stable Microsystems, UK). The apparatus was housed in a controlled environment set at 20° C. and 50% RH. A cylindrical neoprene probe was placed in contact with the hair under a load of 500 g and driven for 40 mm forward and backward at a speed of 10 mm/s to generate a plot of frictional force versus distance. For each test run, the resulting hysteresis loop was integrated to yield a data point with units of grams×millimeters. On averaging these data across all five switches per product, the resulting mean value was used to represent the frictional properties of dry hair following treatment with a test product.

Volume Measurements on Dry Hair

The degree to which individual fibres in a bundle separate on drying was assessed. For switches which undergo more separation, there is more volume in the dry state. When imaged in 2D, the area occupied by the switch is a representation of this volume, thus when comparing switches a larger area is indicative of a larger volume. Smaller area indicates a product delivers lower volume to a switch, suggesting more control and less unwanted attributes like frizz to hair.

Hair switch volume values were determined after treatment with example compositions. Four 2 g/250 mm (10 inch) European hair switches were used for each product to be assessed. Four switches were treated at the same time as a bundle by first washing with a simple, stripping shampoo comprising sodium lauryl ether sulphate and water then applying 2 g of the test product to the bundle, massaging for 1 minute and rinsing for a further minute under tap water set at 37° C. and flowing at 4 liters per minute.

Switches were then individually detangled and combed through before drying at 50° C. The switches were then clipped to a metal frame to hang freely and dry in a humidity controlled room (22° C./20% RH). The switches were photographed and the images analysed for volume. Volume was represented by the area occupied by the switch in mm2. The volume in the dry state was recorded before any further dry stage combing took place. The results are shown below in Table 4.

TABLE 4

| Formulation Name | Silicone emulsion level(% w/w) | Friction (g.mm) | Uncombed Switch Volume (mm$^2$) |
|---|---|---|---|
| Ex B | 0 | 50921 | 12916 |
| Ex 2 | 0.5 | 32433 | 9859 |
| Ex 3 | 1 | 30712 | 10770 |
| Ex 4 | 2 | 25369 | 6462 |
| Ex 5 | 3 | 23238 | 4764 |
| Ex 6 | 4 | 23095 | 3730 |
| Ex C | 0.5 | 35274 | 11205 |
| Ex D | 1 | 34528 | 10574 |
| Ex E | 2 | 28453 | 10007 |
| Ex F | 3 | 27214 | 9429 |
| Ex G | 4 | 24367 | 8825 |

The above results demonstrate that the dimethicone/isohexadecane emulsions (Examples 2 to 6, according to the invention) provide a superior volume down effect to the dimethicone/sunflower oil emulsions (Examples C to G, not according to the invention), when delivered at equivalent active levels and from equivalent conditioning formulations.

The invention claimed is:

1. A process for preparing a hair care composition comprising the steps of:
   forming a conditioning gel phase from a cationic surfactant, a fatty compound, and an aqueous carrier; and
   blending the conditioning gel phase with an aqueous polydimethylsiloxane polymer emulsion;
   wherein:
     the aqueous polydimethylsiloxane polymer emulsion comprises:
       an aqueous continuous phase consisting of water and a blend of non-ionic and cationic surfactants; and
       a dispersed phase consisting of a polydimethylsiloxane polymer and a hydrocarbon oil,
       wherein:
         the polydimethylsiloxane polymer has a dynamic viscosity of 50,000 to 110,000 cP at 25° C.,
         the hydrocarbon oil has a kinematic viscosity of 1 to 35 cSt at 40° C. and a specific gravity of 0.76 to 0.87 at 25° C., and
         the weight ratio of the polydimethylsiloxane polymer to the hydrocarbon oil is 45:55 to 70:30;
     the cationic surfactant used to form the conditioning gel phase is selected from cetyltrimethylammonium chloride (CTAC), behenyltrimethylammonium chloride (BTAC), protonated stearamidopropyldimethylamine, or mixtures thereof;
     the fatty compound used to form the conditioning gel phase is selected from cetyl alcohol, stearyl alcohol, or mixtures thereof; and
     the hydrocarbon oil is selected from saturated, nonpolar straight or branched chain aliphatic or alicyclic hydrocarbons having from 10 to 50 carbon atoms and mixtures thereof.

2. The process of claim 1, wherein the conditioning gel phase is a gel ($L_\beta$) surfactant mesophase obtainable by a process comprising the steps of:
   heating the cationic surfactant, fatty compound and aqueous carrier to form a mixture; and
   controlling the formation of the gel ($L_\beta$) surfactant mesophase by maintaining the temperature of the mixture so that it falls within a range of from 55 to 67° C., in the mixing vessel.

3. The process of claim 1, wherein the cationic surfactant and fatty compound are present in the conditioning gel phase at a weight ratio from 1:1 to 1:10.

4. The process of claim 3, wherein the weight ratio is from 1:2 to 1:5.

5. The process of claim 1, wherein the cationic surfactant of the conditioning gel phase is present at a level from 0.1 to 10 wt % based on the total weight of the hair care composition.

6. The process of claim 1, wherein the fatty compound of the conditioning gel phase is present at a level from 0.01 to 10 wt % based on the total weight of the hair care composition.

7. The process of claim 1, wherein the hydrocarbon oil is selected from mineral oil, isohexadecane, or a mixture thereof.

8. The process of claim 1, wherein the hydrocarbon oil is mineral oil.

9. The process of claim 1, wherein the hydrocarbon oil is isohexadecane.

10. The process of claim 1, wherein the cationic surfactant of the aqueous polydimethylsiloxane polymer emulsion comprises cetyltrimethylammonium chloride.

11. A hair care composition comprising:
a conditioning gel phase comprising a cationic surfactant, a fatty compound, and an aqueous carrier; and
an aqueous polydimethylsiloxane polymer emulsion comprising:
an aqueous continuous phase consisting of water and a blend of non-ionic and cationic surfactants; and
a dispersed phase consisting of a polydimethylsiloxane polymer and a hydrocarbon oil comprising isohexadecane,
wherein:
the polydimethylsiloxane polymer has a dynamic viscosity of 50,000 to 110,000 cP at 25° C., and
the weight ratio of the polydimethylsiloxane polymer to the hydrocarbon oil is 45:55 to 70:30;
wherein:
the cationic surfactant used to form the conditioning gel phase is selected from cetyltrimethylammonium chloride (CTAC), behenyltrimethylammonium chloride (BTAC), protonated stearamidopropyldimethylamine, or mixtures thereof;
the fatty compound used to form the conditioning gel phase is selected from cetyl alcohol, stearyl alcohol, or mixtures thereof;
the hair care composition is formed by a process comprising blending the conditioning gel phase with the aqueous polydimethylsiloxane polymer emulsion.

12. The hair care composition of claim 11, wherein the conditioning gel phase is a gel ($L_\beta$) surfactant mesophase.

13. The hair care composition of claim 11, wherein the cationic surfactant and fatty compound are present in the conditioning gel phase at a weight ratio from 1:1 to 1:10.

14. The hair care composition of claim 13, wherein the weight ratio is from 1:2 to 1:5.

15. The hair care composition of claim 11, wherein the cationic surfactant of the conditioning gel phase is present at a level from 0.1 to 10 wt % based on the total weight of the hair care composition.

16. The hair care composition of claim 11, wherein the fatty compound of the conditioning gel phase is present at a level from 0.01 to 10 wt % based on the total weight of the hair care composition.

17. The hair composition of claim 11, wherein the aqueous polydimethylsiloxane polymer emulsion further comprises a hydrocarbon oil having a kinematic viscosity of 1 to 35 cSt at 40° C. and a specific gravity of 0.76 to 0.87 at 25° C. and is selected from saturated, non-polar straight or branched chain aliphatic or alicyclic hydrocarbons having from 10 to 50 carbon atoms and mixtures thereof.

18. The hair care composition of claim 17, wherein the hydrocarbon oil is a mineral oil.

* * * * *